United States Patent [19]

Löfås

[11] Patent Number: 5,922,594

[45] Date of Patent: Jul. 13, 1999

[54] METHOD OF PRODUCING BILAYER LIPID MEMBRANES

[75] Inventor: Stefan Löfås, Uppsala, Sweden

[73] Assignee: Biacore AB, Uppsala, Sweden

[21] Appl. No.: 08/809,617

[22] PCT Filed: Sep. 26, 1995

[86] PCT No.: PCT/SE95/01099

§ 371 Date: Mar. 25, 1997

§ 102(e) Date: Mar. 25, 1997

[87] PCT Pub. No.: WO96/10178

PCT Pub. Date: Apr. 4, 1996

[30] Foreign Application Priority Data

Sep. 26, 1994 [SE] Sweden .................................. 9403245

[51] Int. Cl.$^6$ .................................................. C12M 1/34
[52] U.S. Cl. ............................ 435/291; 436/13; 422/57; 264/4.1; 424/420; 424/450; 427/2.14
[58] Field of Search .............................. 435/291; 436/13; 422/57; 264/4.1; 424/420, 450; 427/2.14

[56] References Cited

U.S. PATENT DOCUMENTS

| | | | |
|---|---|---|---|
| 5,242,828 | 9/1993 | Bergstrom | 435/291 |
| 5,436,161 | 7/1995 | Bergstrom | 435/291 |
| 5,716,854 | 2/1998 | Lofas | 436/518 |
| 5,763,191 | 6/1998 | Knoll et al. | 435/7.1 |

FOREIGN PATENT DOCUMENTS

| | | |
|---|---|---|
| 2055117 | 5/1992 | Canada . |
| 489465 | 6/1992 | European Pat. Off. . |
| 90 05303 WO90/ | 5/1990 | WIPO . |
| 05303A1 | 5/1990 | WIPO . |
| 93 21528 WO93/ | 10/1993 | WIPO . |
| 21528A1 | 10/1993 | WIPO . |
| 93 22320 | 11/1993 | WIPO . |

OTHER PUBLICATIONS

Brink et al., Biochimica et Biophysica Acta, 1196, 227–230 (1994).
Duschl et al., Biophysical Journal, 67, 1229–1237 (Sep. 1994).
Lang et al., Langmuir, 10, No. 1, 197–210 (1994).
Lang et al., Thin Solid Films, 210/211, 818–821 (1992).
Terrettaz et al., Langmuir, 9, No. 5, 1361–1369 (1993).

Thin Solid Films, 210/211 (1992) pp. 818–812, Self–amssembly of thiuolipid molecular layers on gold surfaces: optical and electrochemical characterization, 1992—Elsevier Sequoia.

Biotechnology: Bridging Research and Applications, Proceedings of the U.S.–Israel Research Conference on Advances in Applied Biotechnology Jun. 24–30, 1990; Haifa, Israel, Daphne Kamely et al, Kluwer Academic Publishers, 1991, pp. 43–61.

Langmuir 1993, 9, 1361–1369, Protein Binding to Supported Lipid Membranes: Investigation of the Cholera Toxin–Ganglioside Interaction by Simultaneous Impedance Spectroscopy and Surface Plasamon Resonance, Samuel Terrettaz, et al Institut de chimie physique II, Ecole Polytechnique Federale de Lausanne, CH–1015, Lausanne, Sqitzerland pp. 1361–1369.

Biosensors Based on Membrane Transport Proteins, Biosensore & Bioelectronics 6 (1991) Elsevier Science Publishers Ltd. England, pp. 233–237, Hans Kiefer et al.

Formation of a Bilayer Liquid Membrance on Rigid Supports: An Approached to BLM–Based Biosensors, Menekhem Zviman & H. Ti Tien, Biosensors & Bioelectronics 6 (1991) pp. 37–42.

Biophysical Journal vol. 67, Sep. 1994, pp. 1229–1237, Biologically Addressable Monolayer Structures Formed by Templates of Sulfur–Bearing Molecules, Claus Duschi et al.

A New Class of Thiolipids for the Attachment of Lipid Bilayers of Gold Surfaces, Holger Lang et al, Institute of Physical Chemistry, Swiss Federal Institute of Technology, CH–1015 Lausanne, Switzerland, Oct. 13, 1993.

Brink et al., "Self assembly of covalently anchored phospholipid supported membranes by use of DODA–Suc–NH-S–lipids," *Biochimica et Biophysica Acta* 1196: 227–230, 1994.

Zot and Pollard, "Motility of Myosin I on Planar Lipid Surfaces," *Methods in Cell Biology* 39: 51–63, 1993.

*Primary Examiner*—Cecilia J. Tsang
*Assistant Examiner*—David Lukton
*Attorney, Agent, or Firm*—Seed and Berry LLP

[57] ABSTRACT

Methods are disclosed for producing a substrate surface supporting a continuous planar bilayer lipid membrane by covalently binding a plurality of micellar of vesicle liposomes, optionally comprising a membrane protein or other biologically active membrane-bound component, to a substrate surface supporting a self-assembled monolayer (SAM) of essentially straight long chain molecules. In one embodiment, the micellar or vesicle liposomes covantly bind to hydrophilic spacer molecules attached to the functional groups of the self-assembled monolayer.

17 Claims, 3 Drawing Sheets

METHOD OF PRODUCING BILAYER LIPID MEMBRANES

CROSS REFERENCE TO RELATED APPLICATION

This application claims priority to Swedish Patent Application No. SE 9403245-5, filed Sep. 26, 1994.

TECHNICAL FIELD

The present invention relates to the preparation of lipid membranes, and more particularly to the preparation of lipid membrane supporting surfaces suitable for use in biosensors.

BACKGROUND OF THE INVENTION

There is currently a general demand for sensors based on the integration of lipid membrane components, such as membrane bound receptor proteins, into planar bilayer lipid membranes, so-called BLM's. Such lipid bilayers may form spontaneously, and are self-assembling under suitable conditions and with suitable surfaces. The BLM's formed may then be used for studying ligand-receptor interactions at the lipid-water interface.

Brian and McConnell, Proc. Natl. Acad. Sci. USA (1984) 81, 6159–6163 describes the spontaneous fusion of phospholipid vesicles to hydrophilic glass surfaces for studies with fluorescence techniques.

Poglitsch and Thompson (1990) Biochemistry 29, 248–254 describes the spontaneous fusion of phospholipid vesicles to hydrophilic glass surfaces by passing the vesicle solution through an assembly of a fused silica substrate and a microscope slide mounted together with a spacer of about 100 μm thickness.

Zot et al. (1992) J. Cell Biol. 116, 367–376 discloses the preparation of planar lipid surfaces in a flow cell and the study of actin filament gliding on the lipid layer by fluorescence microscopy.

Terrettaz et al. (1993) Langmuir 9, 1361–1369 describes the formation of lipid monolayers by the adsorption of alkanethiols with hydrophobic terminal groups in a discontinuous dilution procedure. Interactions with membrane components were studied by surface plasmon resonance and impedance measurements.

Gitler et al., Bridging Research and Applications, 43–61, Eds. D. Kamely et al., 1991 Kluwer Ac Publ., and Vogel et al. (1994) 10, 197–210 disclose approaches to provide for a water layer between the support and the BLM which is desirable in order to obtain conditions suitable for transmembrane proteins. To this end, lipids are modified with an oligoethylene spacer and a thio group (thiol or disulphide). These thiolipids are then anchored to a gold surface together with an unmodified lipid, thereby spontaneously forming a BLM anchored via the thio groups to the metal surface. The oligoethylene spacer was introduced in order to create the desired water layer spacing.

Stelzle, M., et al. (1993) J. Phys. Chem. 97, 2974–2981 discloses the preparation of a bilayer lipid membrane on a biosensor device by first depositing a negatively charged monolayer of a carboxy mercaptan onto gold and then adding vesicles of positively charged dioctadecyldimethylammonium bromide which fuse spontaneously to the negative layer, or alternatively, fusing negatively charged dimyristoylphosphatidylglycerol to the negative layer by the of addition of calcium ions.

DETAILED DESCRIPTION OF THE INVENTION

Figure 1:
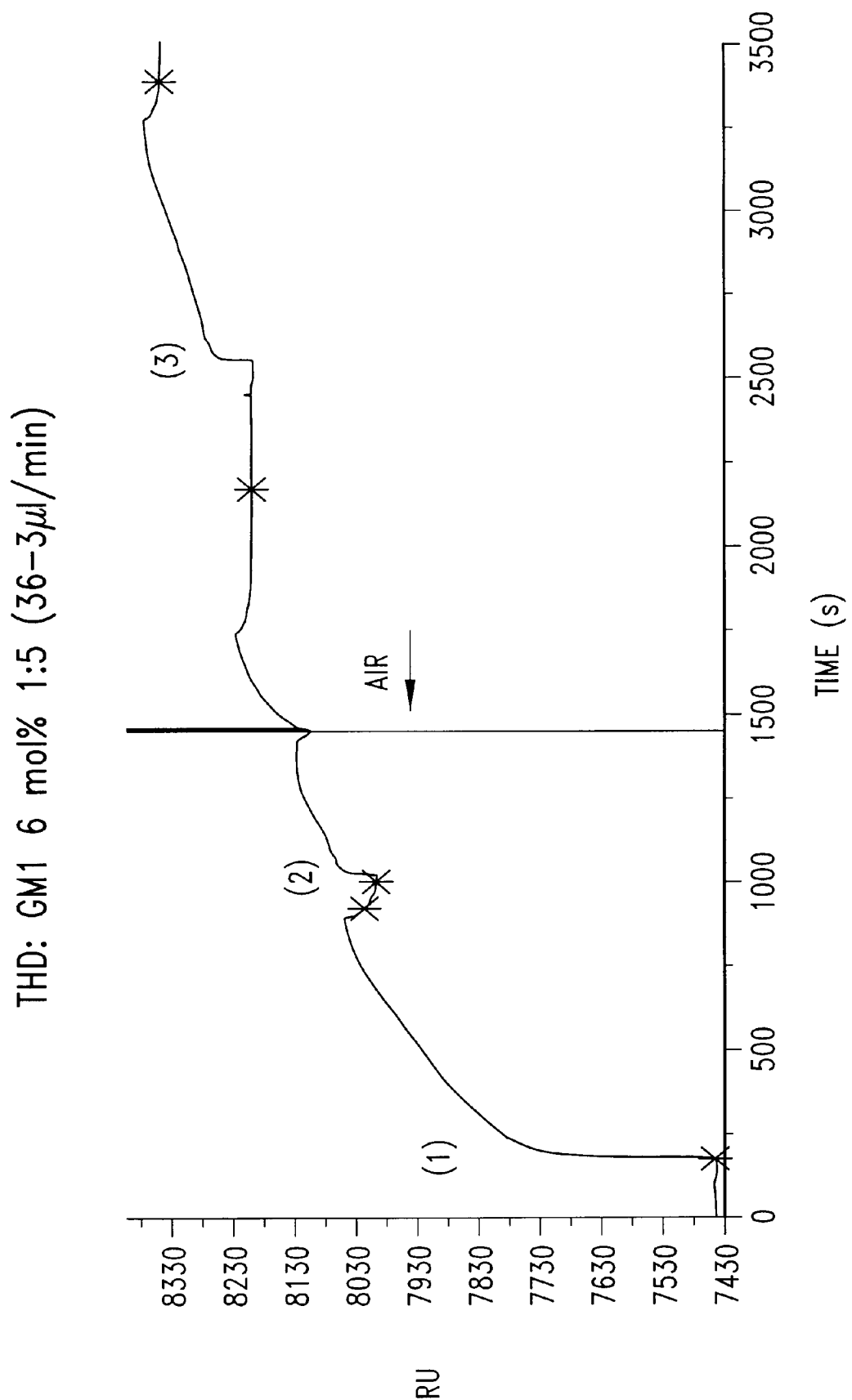
FIG. 1 is a sensorgram showing the response vs. time for three consecutive contactings of liposome solution with a hydrophilic sensor surface to form a lipid bilayer thereon containing ganglioside $G_{M1}$.

The object of the present invention is to provide improvements in the preparation and use of planar BLM's, and more particularly to improve the stability of the formed BLM's. According to the present invention, this and other objects and advantages are achieved by covalently binding the BLM to a self-assembled monolayer on a substrate surface.

The present invention therefore provides a method of producing a substrate surface supporting a continuous planar bilayer lipid membrane by fusing a micellar or vesicle preparation, preferably containing a membrane protein or other biologically active membrane-bound component, to a substrate surface supporting a self-assembled monolayer (SAM) of essentially straight long chain molecules, which method is characterized in that the long chain molecules of the self-assembled monolayer contain functional groups, and that the micellar or vesicle preparation is covalently bound to the self-assembled monolayer via said functional groups.

By anchoring the lipid bilayer to the SAM by covalent bonds, an efficient anchoring process is obtained which insures stability of the bilayer against various environments, such as different buffers and regeneration solutions. Also, in contrast to the approaches described by Gitler et al. and Vogel et al., respectively, supra, on one hand, the fraction of the surface covered by the bilayer can be controlled and a reproducible surface created. On the other hand, bare metal parts uncovered by the bilayer which are highly active in adventitious adsorption or show a hydrophobic character, and therefore may have a negative effect on the formation of a water layer, are avoided.

Surfaces suitable for the preparation of continuous planar bilayer membranes support self-assembled monolayers, so-called SAM's, of essentially straight chain, preferably hydrocarbon derived, molecules, the free ends of which have functional groups selected to provide surface characteristics for optimal membrane formation in terms of stability, functionality, etc. Such surfaces can thus be defined and created for optimal binding of various types of membrane structures by choosing different terminal groups or by mixing molecules with different terminal groups. Optionally, the functionalities of the surface may be arranged to exhibit gradients in one or more directions.

The above-mentioned long chain hydrocarbon derived molecules may, for example, be of the type described in our U.S. Pat. No. 5,242,828 (the entire disclosure of which is incorporated by reference herein), i.e. hydrocarbons, optionally interrupted by heteroatoms, of a length exceeding 10 atoms, and having a functionality in one end for anchoring to the surface, and the desired functionality for the present purposes in the other end.

In an advantageous embodiment, the self-assembled monolayer is selected to provide a hydrophilic surface. A neutral hydrophilic surface may, for example, be provided by a 16-mercaptohexadecanol (THD). Correspondingly, a long chain alkane thiol with a terminal carboxylic group will provide a negatively charged hydrophilic surface. Similarly, a positively charged surface will be obtained by a long chain alkane thiol with a terminal amine group. Other desired surface characteristics may be accomplished by mixtures of two or more of the above alkane thiols. Various other terminal groups are, of course, also conceivable and corresponding alkane thiols may be combined in different ways.

The substrate may e.g. be a metal, such as gold.

The SAM forming molecule, such as an alkane thiol, can be chosen in such a way that the best possible surface is obtained for the creation of the desired hydrophilic environment of the layer between the support and the BLM. For example, if alkane thiols with hydroxy groups form the SAM, a hydrophilic surface is obtained as mentioned above, and the hydroxy groups can then be used for covalent attachment of the lipids. Other functionalities, such as acidic or basic groups can conveniently be introduced via the SAM, optionally by mixtures of different alkane thiols. Also, the metal surface is completely passivated and there is no risk for unwanted adsorption to the metal.

The lipid layer should preferably be imperfect to be able to incorporate transmembrane proteins or other biologically active membrane-bound components.

To prepare a bilayer lipid membrane surface, a micellar or vesicle preparation, preferably containing a membrane protein or other biologically active membrane-bound component, is allowed to covalently fuse, optionally via a hydrophilic spacer, to the lipid layer (SAM), optionally after modification of the latter. The modification of metal surfaces with alkane thiols for biosensor purposes and the advantages of such surfaces have been described in the above-mentioned U.S. Pat. No. 5,242,828.

There are several possible methods for covalently binding the bilayer lipid membrane to the SAM which can be optimized for different purposes. Thus, in one method, the covalent coupling is performed directly to the SAM, using, for example, a reactive phosphatidyl ester which is allowed to react with the alcohol group in a SAM made from a hydroxyalkane thiol.

Alternatively, the SAM is modified with a hydrophilic spacer, such as an oxyethylene group, which is then used for coupling of the lipid. This modification of the SAM can either be made directly by coupling of a suitable oligoethylene molecule or by first modifying the alkane thiol with an oligoethylene tail and then introducing it on the surface together with an unmodified alkane thiol in order to form a mixed SAM. Using this approach, the fraction of surface modified with oligoethylene chains can easily be varied and controlled in order to create the optimal conditions.

A further possibility is to modify the lipid with the hydrophilic spacer and then couple the modified lipid to the SAM via a functionality on the hydrophilic spacer that is reactive towards the SAM.

By using a SAM composed of a mixture of two different alkane thiols where only one of the alkane thiols has reactivity for the lipid (optionally modified with a hydrophilic spacer), the degree of modification can easily be controlled to the desired level.

It is readily understood that there are numerous of alternative covalent attachment methods. The SAM can be modified with a nucleophilic group like an amine (primary, secondary or tertiary), either directly or via a spacer such as the oxyethylene group mentioned above. Also nucleophilic groups like thiols, hydrazides, carboxylates are possible alternatives. In those cases the liposomes should contain lipids where the polar head groups are modified with electrophilic groups like phosphatidyl esters, or activated carboxylic based electrophiles such as esters or acid halides. Also lipid head groups containing carbonyl, epoxide, vinyl groups are conceivable as reactive counterparts to the nucleophiles on the surface. For selective reactions towards thiol functions, pyridyl disulfides, maleimides or haloacetate groups are preferred.

Alternatively, the nucleophilic group can be placed in the liposome, such as an amine or thiol containing lipid. Exemplary of these are lipids with phosphatidylethanolamine head groups, providing a reactive primary amine. In those cases, the SAM should be modified with an electrophilic functionality such as an activated carboxylic ester or the like, optionally via a spacer linkage such as an oxyethylene group. Other pairs of nucleophilic/-electrophilic groups are also possible alternatives here.

The restrictions for choosing functionalities for the formation of a covalent anchoring of the lipid bilayer is limited only by the stability of the SAM layer and the liposomes. For example, as liposomes normally are formed in water solution and the fusion to the surface is intended to take place under aqueous conditions at 5 to 50° C., the choice of suitable reactants must be compatible with such conditions. This is readily understood to those skilled in the art, and also that the listing of possible alternatives above is not complete, but that a number of alternative chemical functions can be used for the formation of covalent bonds.

The continuous planar membranes prepared according to the invention may conveniently be used for studies of interactions with membrane-bound components by means of surface sensing techniques. In this case, the membrane is preferably formed in a flow cell using a controlled laminar flow, and the subsequent interaction studies are performed in the same flow cell.

This method offers several advantages. Thus, forming the membrane in situ in a flow cell system with a combined flow and measuring cell increases the reproducibility, speeds up the process and reduces the risk of contamination and destruction of the membrane in the following interaction studies. Further, the use of a surface sensing technique permits the formation of the membrane to be followed in real-time. This is, of course, also advantageous in the subsequent interaction studies with regard to reproducibility, rapidness and for quantification reasons.

The term "surface sensing techniques" as used herein refers to techniques where the adsorption of the lipid layer to the surface as well as subsequent interactions with the lipid layer cause measurable changes of a property of the sensing surface. Exemplary of such techniques are those based on mass detecting methods, such as piezoelectric, optical, thermo-optical and surface acoustic wave (SAW) methods, and electrochemical methods, such as potentiometric, conductometric, amperometric and capacitance methods.

Among optical methods may particularly be mentioned those that detect mass surface concentration or refractive index, such as reflection-optical methods, including both internal and external reflection methods, e.g. ellipsometry and evanescent wave spectroscopy (EWS), the latter including surface plasmon resonance spectroscopy (SPRS), Brewster angle refractometry, critical angle refractometry, frustrated total reflection (FTR), evanescent wave ellipsometry, scattered total internal reflection (STIR), optical wave guide sensors, evanescent wave based imaging, such as critical angle resolved imaging, Brewster angle resolved imaging, SPR angle resolved imaging, etc., as well as methods based on evanescent fluorescence (TIRF) and phosphorescence.

In the Example described below, a commercial instrument based on surface plasmon resonance (SPR) detection was used (BIAcore™, Pharmacia Biosensor AB, Uppsala, Sweden). The phenomenon of SPR is well known. In brief, SPR is observed as a dip in intensity of light reflected at a specific angle from the interface between an optically transparent material, e.g. glass, and a thin metal film, usually silver or gold, and depends on among other factors the refractive index of the medium (e.g. a sample solution) close to the metal surface. A change of refractive index at the metal surface, such as by the adsorption or binding of material thereto, will cause a corresponding shift in the angle at which SPR occurs. To couple the light to the interface such that SPR arises, two alternative arrangements are used, either a metallized diffraction grating (Wood's effect), or a metallized glass prism or a prism in optical contact with a metallized glass substrate (Kretschmann effect). For further details on SPR, reference is made to our WO 90/05295. Applications of the invention are described below.

The lipid bilayers are preferably formed from liposomes (spherical vesicles), for example, from phospholipids.

In the following, the invention is illustrated by a non-limiting Example which describes the fusion step in the method of the invention.

EXAMPLE 1

A gold-coated glass surface was placed in a petri dish and a 5 mM solution of 16-mercaptohexadecanol in ethanol/water 80/20 was poured over the surface. The petri dish was provided with a cover and incubated on a shaker incubator at 40° C. for 20 minutes. The surface was washed with 5×50 ml ethanol, 50 ml ethanol/water 80/20, and 5×50 ml water. The hydrophilic properties of the surface were confirmed by measuring the contact angles of water, giving values of <10°. (Unmodified gold surfaces show contact angles of typically >75°, due to uncontrolled vapour contamination of the surface by nonpolar compounds.) The sensor surface was introduced into a commercial biosensor instrument, BIAcore™ (Pharmacia Biosensor AB, Uppsala, Sweden), which is an SPR measuring instrumentation with flow cells. This instrument enables monitoring of mass changes (adsorptions and desorptions) in the vicinity of the sensor surface as a function of time under constant flow conditions.

Liposomes composed of 50 mole % dipalmitoyl phosphatidylcholine, 40 mole % dipalmitoyl phosphatidylethanolamine, 10 mole % cholesterol and 6 mole % ganglioside $G_{M1}$ were prepared by detergent depletion with gel chromatography according to the procedure described by Mimms et al., Biochemistry (1980) 20, 833–840. Liposomes with a diameter of 50–150 nm were obtained and used in the following.

Figure 2:
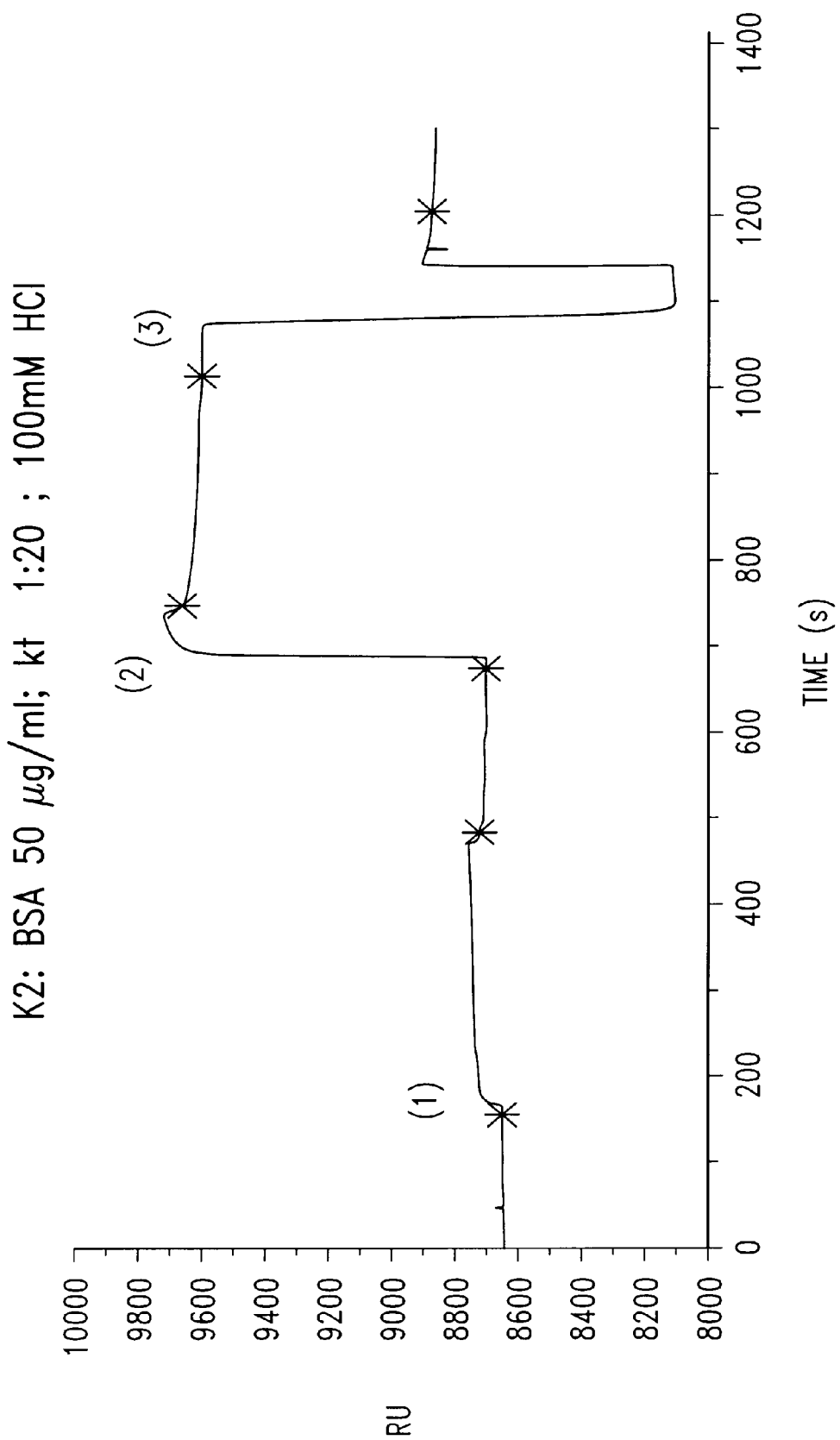
FIG. 2 is a corresponding sensorgram to that in FIG. 1 and shows the response when sequentially contacting the lipid surface with negative control (BSA), cholera toxin, and hydrochloric acid.

A 20 $\mu$M solution of the liposomes (in running buffer: 10 mM HEPES with 0.15 m sodium chloride, pH 7.4) was injected over the hydrophilic surface. FIG. 1 shows the response curve obtained after three consecutive injections of the liposome solution, (1), (2) and (3). The plateaus after the end of sample pulses (2) and (3) indicate the formation of a stable lipid layer on the sensor surface. FIG. 2 shows the injection of (1) bovine serum albumin (50 $\mu$g/ml in running buffer) as a negative control, (2) cholera toxin, subunit B (50 $\mu$g/ml in running buffer) and (3) 100 mM hydrochloric acid. The albumin injection indicates very low non-specific binding to the modified surface (44 resonance units, RU≈44 pg/mm$^2$). The cholera toxin injection shows the specific binding to the ganglioside $G_{M1}$ incorporated in the lipid layer (941 RU≈0.94 ng/mm$^2$). The injection of the hydrochloric acid illustrates the regeneration of the lipid surface by disruption of the specific interaction between the cholera toxin and the ganglioside. By the one minute pulse, 80% of the bound cholera toxin is desorbed from the surface, which then is ready for a renewed binding (not shown).

Figure 3:
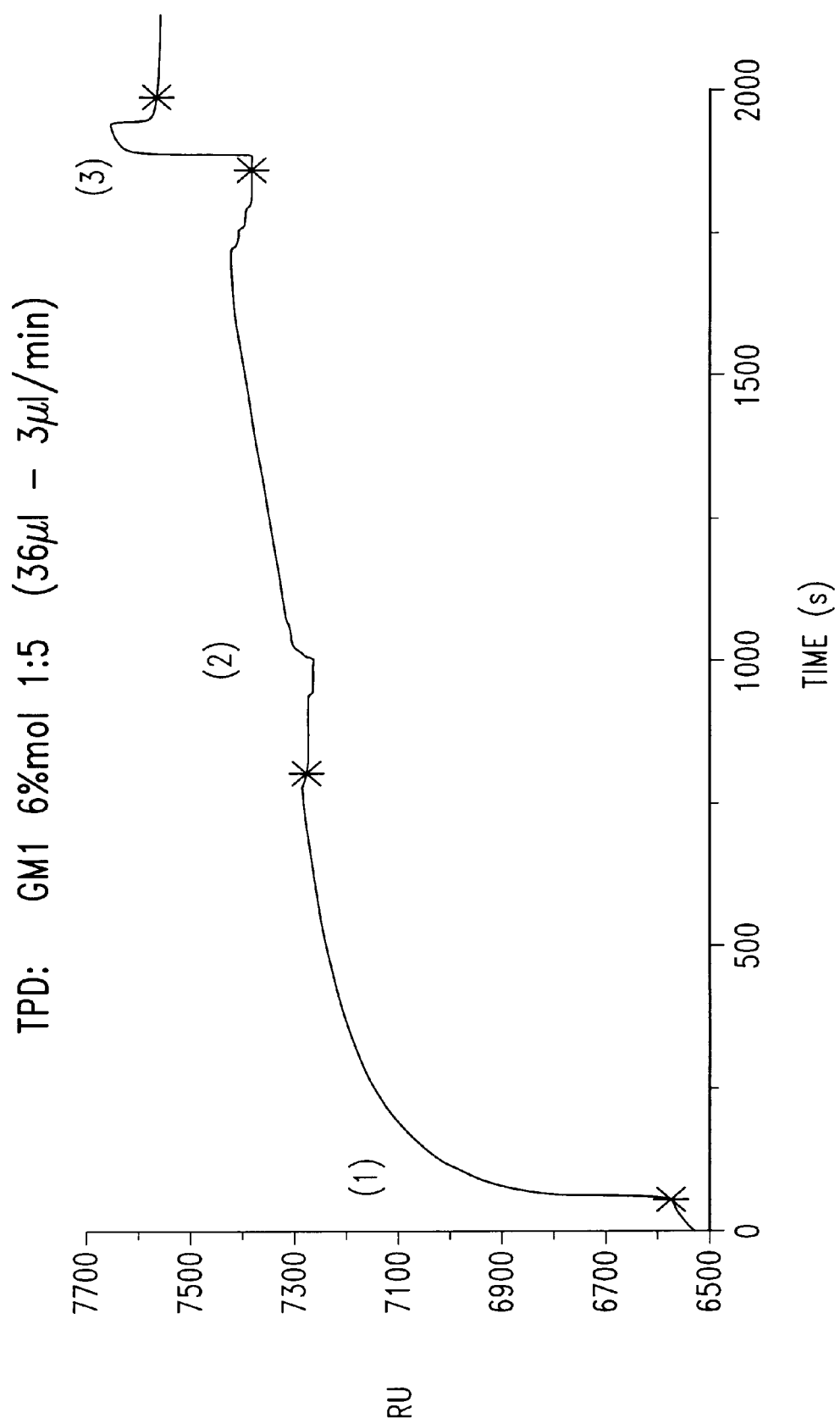
FIG. 3 is a corresponding sensorgram to those in FIGS. 1 and 2 and shows the response for the formation of a highly hydrophobic lipid layer and the subsequent contacting of the lipid layer with cholera toxin.

As a comparison, a gold-coated surface was modified with pentadecan-1-thiol according to the same procedure as described above. This modified surface is highly hydrophobic, with a contact angle of >105°. FIG. 3 shows the injections [(1) and (2)] of two consecutive pulses of the liposome solution as described above followed by (3) the injection of the cholera toxin solution. Although FIG. 3 indicates the formation of a lipid layer from the liposome solution, the specific activity of this layer for binding the cholera toxin is much lower than for the situation described above (182 and 941, RU, respectively). This example illustrates the importance of the surface characteristics for the formation of functionally active lipid layers. In contrast to the hydrophobic surface, the hydrophilic surface is likely to yield lipid bilayers with resemblance to the biological membrane and thus a high functional activity.

The invention is, of course, not restricted to the embodiments described above, but encompasses modifications and variants obvious to the skilled person and covered by the general inventive concept as defined in the following claims.

I claim:

1. A method of producing a substrate surface supporting a bilayer lipid membrane, comprising the steps of:
    providing a substrate, wherein the substrate has coated thereon a self-assembled monolayer of essentially straight long chain molecules having functional groups;
    contacting the substrate with an aqueous solution comprising micellar of vesicle liposomes such that a plurality of the micellar or vesicle liposomes covalently bond to the functional groups of the self-assembled monolayer so as to form the substrate surface supporting the bilayer lipid membrane.

2. The method according to claim 1, wherein the micellar or vesicle liposomes covalently bond to hydrophilic spacer molecules, wherein the hydrophilic spacer molecules are attached to the functional groups of the self-assembled monolayer.

3. The method according to claim 1, wherein the micellar or vesicle liposomes comprise a membrane protein.

4. The method according to claim 1 or 2, wherein the straight long chain molecules are derived from hydrocarbons.

5. The method according to claim 4, wherein the straight long molecules comprise alkane thiols.

6. The method according to claim 5, wherein the alkane thiols have at least ten atoms in their chain.

7. The method according to claim 1, wherein the straight long chain molecules are selected to provide a hydrophilic surface.

8. The method according to claim 7, wherein the straight long chain molecules comprise hydroxyalkane thiols.

9. The method according to claim 1, wherein the straight long chain molecules comprise a mixture of molecules with different functionalities.

10. The method according to claim 1, wherein the straight long chain molecules are bounded to a metal.

11. The method according to claim 10, wherein the metal is gold.

12. The method according to claim 1, wherein the step of contacting the substrate with the aqueous solution comprising micellar or vesicle liposomes is carried out in a flow cell using a controlled laminar flow.

13. The method according to claim 1, wherein the method further comprisis monitoring the formation of the bilayer lipid membrane by a surface technique that detects measurable changes in a property associated with the substrate.

14. The method according to claim 13, wherein the method further comprises monitoring molecular interactions between an analyte and the bilayer lipid membrane by the surface sensing technique.

15. The method according to claim 13 or 14, wherein the surface sensing technique is based on mass sensing.

16. The method according to claim 13 or 14 wherein the surface sensing technique is based on evanescent wave sensing.

17. The method according to claim 13 or 14 wherein the surface sensing technique is based on surface plasmon resonance.

* * * * *